United States Patent Office

Re. 27,822
Reissued Nov. 27, 1973

27,822

1-SUBSTITUTED PHENOXY-2-HYDROXY-3-ISOPROPYLAMINO-PROPANES

Herbert Koppe, Ingelheim am Rhein, Albrecht Engelhardt, Mainz, Gerhard Ludwig, Lippamsdorf, and Karl Zeile, Ingelheim am Rhein, Germany, assignors to Boehringer Ingelheim, G.m.b.H., Ingelheim am Rhein, Germany No Drawing. Original No. 3,459,782, dated Aug. 5, 1969, Ser. No. 619,141, Feb. 28, 1967, which is a continuation-in-part of Ser. No. 391,012, Aug. 20, 1964. Application for reissue July 6, 1971, Ser. No. 160,223

Claims priority, application Germany, Aug. 26, 1963, B 73,262; June 24, 1966, B 87,707; Dec. 30, 1966, B 90,543; Feb. 6, 1967, B 91,070

Int. Cl. C07c *121/50, 121/66*

U.S. Cl. 260—465 E 10 Claims

Matter enclosed in heavy brackets [ ] appears in the original patent but forms no part of this reissue specification; matter printed in italics indicates the additions made by reissue.

ABSTRACT OF THE DISCLOSURE 1-substituted phenoxy-2-hydroxy-3-N-isopropyl-aminopropanes and acid addition salts thereof, possessing bradycardia activity and N-isopropyl-nor adrenaline antagonistic activity.

The present application is a continuation-in-part application of copending, commonly assigned, application Ser. No. 391,012, filed Aug. 20, 1964 now abandoned.

The invention relates to novel 1-aryloxy-2-hydroxy-3-isopropylamino-propanes and acid addition salts thereof, as well as to various methods of preparing these compounds.

More particularly, the present invention relates to racemic 1-substituted phenoxy-2-hydroxy-3-isopropyl-aminopropane of a formula selected from the group consisting of

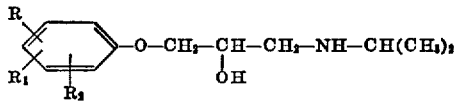

(I)

and

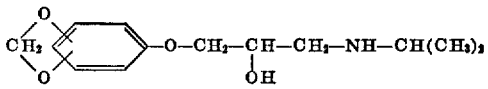

(Ia)

wherein R is selected from the group consisting of hydrogen, halogen, alkyl and alkoxy to 1 to 4 carbon atoms, hydroxyalkyl of 1 to 4 carbon atoms, hydroxycarbonyl, alkoxycarbonyl of 1 to 4 carbon atoms, alkenyl and alkynyl of 2 to 4 carbon atoms, thio alkyl of 1 to 4 carbon atoms and cyan, $R_1$ is selected from the group consisting of $-(CH_2)_x-CN$ and $-(CH_2)_x-NH_2$, x is an integer from 0 to 3 and $R_2$ is selected from the group consisting of hydrogen, halogen and alkyl or alkoxy of 1 to 4 carbon atoms, their optically active isomers and non-toxic, pharmaceutically acceptable acid addition salts of said racemates and of said optically active isomers.

The compounds according to the present invention may be prepared by a number of different methods involving known chemical reaction principles; however, among these, the following methods have been found to be most convenient and efficient:

Method A

By reacting an epoxide of the formula

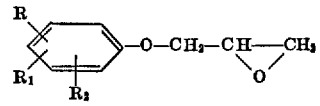

(II)

or

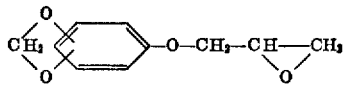

(IIa)

where the R's have the same meanings as in Formula I, with isopropylamine in the presence of an inert solvent, such as ethanol.

Method B

By reacting a 1-substituted phenoxy-2-hydroxy-3-halo propane of the formula

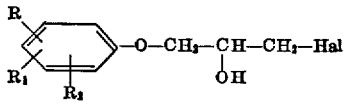

(III)

or

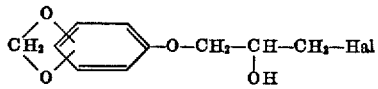

(IIIa)

wherein the R's have the same meanings as in Formula I, and Hal is halogen, with isopropylamine in the presence of an inert solvent, such as ethanol.

Method C

By reacting a 1 - substituted phenoxy - 2 - hydroxy - 3-amino-propane of the formula

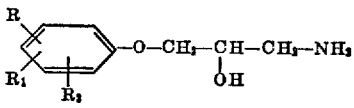

(IV)

or

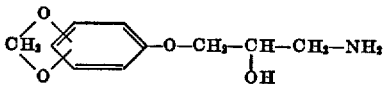

(IVa)

wherein the R's have the same meanings as in Formula I, with an isopropyl halide.

Method D

By hydrolizing an oxazolidinone of the formula

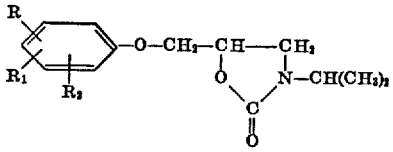

(V)

or

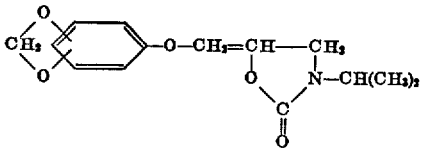

(Va)

wherein the R's have the same meanings as in Formula I.

Method E

By reacting a substituted phenolate of the formula

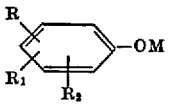

(VI)

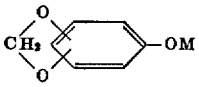

(VIa)

wherein the R's have the same meanings as in Formula I and M is a monovalent cation, preferably an alkali metal, with a 1-halo-2-hydroxy-3-isopropylamino-propane.

Method F

By hydrogenating a 1-substituted phenoxy 2-hydroxy-3 benzylisopropylamino-propane of the formula

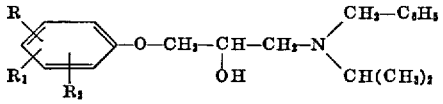

(VII)

or

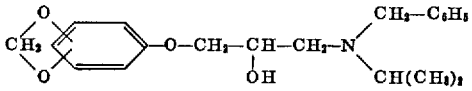

(VIIa)

wherein the R's have the same meanings as in Formula I.

Method G

By reducing a ketone of the formula

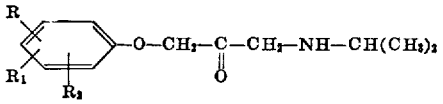

(VIII)

or

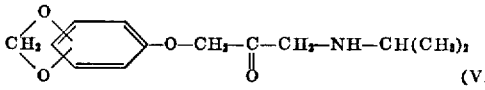

(VIIIa)

wherein the R's have the same meanings as in Formula I, with catalytically activated hydrogen or a boranate, such as aluminum boranate.

The starting compounds of the Formulas II to VIII and IIa to VIIIa for the above methods are known compounds or may readily be prepared by known methods. For example, the substituted 1-phenoxy-2,3-epoxy propanes of Formula II may be prepared by reacting a corresponding substituted phenol under alkaline conditions with a 1-halo-2,3-epoxy-propane such as epichlorohydrin. Most of the corresponding phenols are known in the prior art and they are easily obtainable by conventional methods. Cyanophenols, particularly those with alkyl and/or alkoxy groups, may be prepared by splitting off water from the correspondingly substituted phenolic benzaldoximes which are prepared from known phenolic benzaldehydes. Cyanophenols with an allyl substituent are obtained by reacting the cyanophenol with allyl bromide with rearrangement of the intermediate allyl ether into the final product. Halocyanophenols are obtained by reacting the cyanophenol with a hydrogen halide in the presence of $H_2O_2$. Cyanomethylphenols can be made by introducing a nitro group into a benzylnitrile and converting it into a phenol group by reducing, diazotizing and boiling down. The aminomethylphenols are prepared by reduction of the corresponding cyanomethylphenol. Other processes are described in Belgian Patent No. 641,133, British Patent No. 894,189 and in the literature.

The free bases of the Formulas I and Ia obtained by any of the above methods, A through G, may subsequently be transformed into non-toxic, pharmacologically acceptable acid addition salts by convenional methods, that is, by acidifying a solution of the free base with the desired acid and recovering the acid addition salt by evaporation of the solvent or by precipitation, for instance.

Examples of non-toxic, pharmacologically acceptable acid addition salts of the bases are those formed with hydrochloric acid, hydrobromic acid, sulfuric acid, phosphoric acid, methane sulfonic acid, acetic acid, lactic acid, tartaric acid, ascorbic acid, 8-chlorotheophylline and the like.

The following examples further illustrate the present invention and will enable others skilled in the art to understand it more completely. It should be understood, however, that our invention is not limited to the specific examples given below.

EXAMPLE I

Preparation of 1-(2-methoxy-4-cyanophenoxy)-2-hydroxy-3-isopropylamino-propane.HCl 15.4 g. (0.075 mol) of 1-(2-methoxy-4-cyanophenoxy)-2,3-epoxy-propane were dissolved in 100 ml. of ethanol and after 17.7 g. (0.3 mol) of isopropylamine were added, the mixture was heated to 50–60° C. for one hour. Then it was heated for two hours under reflux and the solvent was distilled off (in vacuo) and the residue was mixed with ether. After addition of dilute hydrochloric acid, it was shaken vigorously and the aqueous phase was separated and made alkaline with NaOH. The precipitating oily base was taken up in ether and the ethereal phase was separated, washed with water and dried over $MgSO_4$. Then, the ether was distilled off and the solid residue recrystallized from ethylacetate/petroleum ether. The thus purified free base was dissolved in ethanol, ethereal HCl added and the precipitate was sucked off to obtain 8.2 g. (37% of theory) of 1-(2-methoxy-4-cyanophenoxy)-2-hydroxy-3-isopropylamino-propane hydrochloride having a melting point of 135–137° C.

EXAMPLE II

Preparation of 1-(2-methoxy-5-cyanophenoxy)-2-hydroxy-3-isopropylamino-propane.HCl 20 g. (0.1 mol) of 1-(2-methoxy-5-cyanophenoxy)-2,3-epoxy-propane were dissolved in 150 ml. of methanol and after 17.7 g. (0.3 mol) of isopropylamine were added and after standing for one hour at room temperature, the mixture was heated under reflux. Then the solvent was distilled off in vacuo, the residue was digested with dilute HCl and the not completely clear solution was filtered over Celite. The thus purified aqueous phase was made alkaline with NaOH and the precipitated base was extracted by ether. The ethereal phase was washed with water and after drying over $MgSO_4$ was evaporated in vacuo. The solid residue was recrystallized from ethylacetate/petroleum ether to obtain 10.5 g. of the free base which was dissolved in ethanol, acidified with ethereal HCl, filtered hot and then some ether was added. The resulting crystalline precipitate was filtered and dried to obtain 10.7 g. (36% of theory) of 1-(2 - methoxy - 5-cyanophenoxy)-2-hydroxy - 3 - isopropylamino-propane hydrochloride having a melting point of 127 to 130° C.

EXAMPLE III

Preparation of 1-(2-methoxy-5-cyanophenoxy)-2-hydroxy-3-isopropylamino-propane.HCl Using the process of Example I, 19.5 g. (0.095 mol) of 1-(2 - methoxy-6-cyanophenoxy)-2,3-epoxypropane in methanol were reacted with 17.7 g. (0.3 mol) of isopropylamine. By dissolution of the purified, solid base in ethanol, after addition of ethereal HCl, 14.4 g. (50% of theory) of crystalline 1-(2 - methoxy-6-cyanophenoxy)-2-hydroxy-3-isopropylaminopropane hydrochloride having a melting point of 148–151° C. were obtained.

EXAMPLE IV

Preparation of 1-(2-cyano-5-methoxyphenoxy)-2-hydroxy-3-isopropylamino-propane.HCl Using the process of Example II, 17.5 g. (0.088 mol) of 1-(2-cyano-5-methoxy)-2,3-epoxypropane in 100 ml. of methanol were reacted with isopropylamine. 9.5 g. of the recrystallized free solid base having a melting point of 71 to 73° C. were dissolved in ethanol, mixed with ethereal hydrochloric acid to obtain 9.8 g. (38% of theory) of purely white 1-(2-cyano-5-methoxyphenoxy)-2-hydroxy-3-isopropylaminopropane hydrochloride having a melting point of 147–149° C.

EXAMPLE V

Preparation of 1-(2-allyl-4-cyanophenoxy)-2-hydroxy-3-isopropylamino-propane.HCl 16 g. (0.0745 mol) of 1-(2-allyl-4-cyanophenoxy)-2,3-epoxypropane were reacted with isopropylamine in ethanol using the procedure of Example II. The purified base (13 g.) having a melting point of 92–94° C. was dissolved in ethanol and acidified with ethereal HCl to obtain 12.5 g. of 1-(2-allyl-4-cyanophenoxy)-2-hydroxy-3-isopropylaminopropane hydrochloride (54% of theory) having a melting point of 140–142° C.

EXAMPLE VI

Preparation of 1-(4-cyanomethylphenoxy)-2-hydroxy-3-isopropylamino-propane.HCl 21.2 g. (0.112 mol) of 1-(4-cyanomethylphenoxy)-2,3-epoxy-propane were reacted in methanol with isopropylamine using the procedure of Example II. The solid base (22.2 g.) was mixed in ethanol with ethereal HCl to obtain 1-(4-cyanomethylphenoxy)-2-hydroxy-3-isopropylamino-propane hydrochloride having a melting point of 155–158° C.

EXAMPLE VII

Preparation of 1-(2-cyanomethylphenoxy)-2-hydroxy-3-isopropylamino-propane.HCl 7.8 g. (0.041 mol) of 1-(2-cyanomethylphenoxy)-2,3-epoxy-propane were reacted with isopropylamine in ethanol using the procedure of Example II. The isolated solid base (7.0 g.) was dissolved in ethanol and 1-(2-cyanomethylphenoxy) - 2 - hydroxy-3-isopropylamino-propane hydrochloride was precipitated with ethereal hydrochloric acid. Its melting point was 119–121° C.

EXAMPLE VIII

Preparation of 1-(2-amino-5-methoxyphenoxy)-2-hydroxy-3-isopropylamino-propane.2HCl 5.68 (0.02 mol) of 1-(2-nitro-5-methoxyphenoxy)-2-hydroxy-3-isopropylamino-propane were dissolved in 200 ml. of methanol and hydrogenated at room temperature over Raney-nickel. After sucking off the catalyst, the clear solution was evaporated in vacuo, whereby 5.6 g. of basic residue was obtained. The residue was dissolved in ethanol, mixed with ethereal HCl and the resulting crystalline 1-(2-amino-5-methoxyphenoxy) - 2 - hydroxy-3-isopropylamino-propane dihydrochloride was isolated. It was recrystallized from ethanol under addition of ether to obtain 3.5 g. (53% of theory) having a melting point of 223–225° C.

EXAMPLE IX

Preparation of 1-(3-cyano-4-chlorophenoxy)-2-hydroxy-3-isopropylaminopropane.HCl 9.36 g. (0.04 mol) of 1-(3-cyanophenoxy)-2-hydroxy-3-isopropylamino-propane were dissolved in 64 ml. of concentrated HCl and after 4.5 g. of $H_2O_2$ of 30% were dropped into it, the mixture was heated to 60° C. When the temperature had reached 65° C., it was stirred for 30 minutes at this temperature. Then, the cooled down batch was made alkaline with NaOH. The precipitated base was extracted with ether and the ethereal phase was separated, washed with water and dried over $MgSO_4$. After the ether was evaporated, a solid basic residue remained, which was recrystallized from ethylacetate with addition of petroleum ether to obtain 4.5 g. of 1-3-cyano-4-chlorophenoxy)-2-hydroxy-3-isopropylamino - propane having a melting point of 118–122° C. The said base was dissolved in ethanol and mixed with ethereal HCl whereby the crystalline hydrochloride precipitated. After filtering and drying, 2.9 g. (24% of theory) of the product having a melting point of 175–177° C. were obtained.

EXAMPLE X

Preparation of 1-(2-cyano-4-chlorophenoxy)-2-hydroxy-3-isopropylaminopropane.HCl 3.51 g. (0.015 mol) of 1-(2-cyanophenoxy)-2-hydroxy-isopropylamino-propane were chlorinated and processed in $HCl/H_2O_2$ as in Example IX. The isolated base (2.2 g.) melted at 91–94° C. It was dissolved in ethanol and mixed with ethereal HCl to obtain 2.3 g. (48% of theory) colourless crystals of 1-(2-cyano-4-chlorophenoxy)-2-hydroxy-3-isopropylamino-propane hydrochloride having a melting point of 167–168° C.

EXAMPLE XI

Preparation of 1-(3-cyano-4-bromophenoxy)-2-hydroxy-3-isopropylaminopropane.HCl 7.02 g. (0.03 mol) of 1-(3-cyanophenoxy)-2-hydroxy-3-isopropylamino-propane were dissolved in 50 ml. of 50% HBr and heated to 45° C. 3.4 g. (0.03 mol) of 30% $H_2O_2$ were stirred in slowly, whereby the temperature rose to approximately 70° C. When the addition was finished, the mixture was heated to 60° C. for an hour. Then, water was added and the mixture was made alkaline with NaOH. The base was shaken with ether and the ethereal phase was separated, washed with water, dried with $MgSO_4$ and the ether was distilled off. The solid residue was recrystallized from ethyl acetate with addition of petroleum ether to obtain 2.8 g. of 1-(3-cyclo-4-bromophenoxy)-2-hydroxy-3-isopropylamino-propane having a melting point of 120–128° C. The said base was dissolved in ethanol, mixed with ethereal HCl and the separated crystal was filtered to obtain 3.9 g. (37% of theory) of the corresponding hydrochloride having a melting point of 194–196° C.

EXAMPLE XII

Preparation of 1-(2-cyano-4-bromophenoxy)-2-hydroxy-3-isopropylamino-propane.HCl Using the procedure of Example XI, 2.34 g. (0.01 mol) of 1-(2-cyanophenoxy)-2-hydroxy-3-isopropylaminopropane were brominated with $HBr/H_2O_2$ to obtain 1.5 g. of 1-(2-cyano-4-bromophenoxy)-2-hydroxy-2-isopropylaminopropane having a melting point of 92–93° C. The base dissolved in ethanol was treated with ethereal HCl to obtain 1.5 g. (43% of theory) of the corresponding hydrochloride having a melting point of 167 to 169° C.

EXAMPLE XIII

Preparation of 1-(4-aminomethylphenoxy)-2-hydroxy-3-isopropylamino-propane.2HCl 22.2 g. (0.095 mol) of 1-(4-cyanophenoxy)-2-hydroxy-3-isopropylamino-propane were dissolved in 200 ml. of methanol. Ammonia was added thereto and the mixture was hydrogenated over Raney-nickel at a hydrogen pressure of 21 atmospheres at 20° C. After filtering off the catalyst, the solvent was distilled off in vacuo and the oily residue was dissolved in ethanol and acidified with alcoholic HCl. The solution was filtered hot and then cooled to obtain 18.1 g. (61.5% of theory) of 1-(4-amino - methylphenoxy) - 2 - hydroxy-3-isopropylamino-propane dihydrochloride in the form of colorless crystals having a melting point of 241 to 244° C.

EXAMPLE XIV

Preparation of 1-(3-aminomethylphenoxy)-2-hydroxy-3-isopropylamino-propane.2HBr 13 g. (0.055 mol) of 1-(3-cyanophenoxy)-2-hydroxy-3-isopropylamino-propane were hydrogenated and worked up as in Example XIII. The basic residue was dissolved in isopropanol and treated with HBr and filtered to obtain 12.5 g. (57% of theory) of colorless 1-(3-amino-methylphenoxy)-2-hydroxy-3-isopropylamino-propane dihydrobromide having a melting point of 178 to 181° C.

EXAMPLE XV

Preparation of 1-(2-chloro-5-aminophenoxy)-2-hydroxy-3-isopropylamino-propane.2HCl Using the process of Example VIII, (1-2-chloro-5-nitrophenoxy)-2-hydroxy-3-isopropylamino-propane was hydrogenated and worked up to obtain 1-(2-chloro-5-amino-phenoxy)-2-hydroxy-3-isopropylamino-propane dihydrochloride having a melting point of 175–178° C.

EXAMPLE XVI

Preparation of 1-(2-allyl-6-cyanophenoxy)-2-hydroxy-3-isopropylamino-propane

Using the procedure of Example II, 1-(2-allyl-6-cyanophenoxy)-2,3-epoxy-propane was reacted with isopropylamine to obtain 1-(2-allyl-6-cyanophenoxy)-2-hydroxy-3-isopropylamino-propane having a melting point of 52 to 54° C.

EXAMPLE XVII

Preparation of 1-(2-allyl-5-cyanophenoxy)-2-hydroxy-3-isopropylamino-propane.HCl Using the procedure of Example II, 1-(2-allyl-5-cyanophenoxy)-2,3-epoxy-propane was reacted with isopropylamine to obtain 1-(2-allyl-5-cyanophenoxy)-2-hydroxy-3-isopropylamino-propane hydrochloride having a melting point of 150–152° C.

EXAMPLE XVIII

Preparation of 1-(4-aminophenoxy)-2-hydroxy-3-isopropylamino-propane.2HCl

Using the procedure of Example VIII, 1-(4-nitrophenoxy)-2-hydroxy - 3 - isopropylamino-propane was reacted with Raney-nickel/$H_2$ to obtain 1-(4-aminophenoxy)-2-hydroxy-3-isopropylamino-propane dihydrochloride having a melting point of 240–241° C.

EXAMPLE XIX

Preparation of 1-(3,4-methylenedioxyphenoxy)-2-hydroxy-3-isopropylamino-propane.HCl 0.1 mol of 1 - (3,4-methylenedioxyphenoxy)-3-chloropropanol-2 was dissolved in 75 cc. of ethanol and 0.3 mol of isopropylamine was added to the solution. After the exothermic reaction had subsided, the reaction mixture was allowed to stand overnight at room temperature after which it was heated at 60° C. for 3 hours. The ethanol was distilled off in vacuo and the residue was worked up to obtain 1-(3,4-methylenedioxyphenoxy)-2-hydroxy-3-isopropylamino-propane. The free base was then converted into its hydrochloride which had a melting point of 127–127.5° C.

EXAMPLE XX

Preparation of 1-(2-aminophenoxy)-2-hydroxy-3-isopropylamino-propane.2HCl

Using the procedure of Example VIII, 1-(2-aminophenoxy)-2-hydroxy-3-isopropylamino-propane was prepared from 1-(2-nitrophenoxy)-2-hydroxy-3-isopropylamino-propane. Its dihydrochloride had a melting point of 216–219° C.

EXAMPLE XXI

Preparation of 1-(3-aminophenoxy)-2-hydroxy-3-isopropylamino-propane

Using the procedure of Example VIII, 1-(3-nitro-phenoxy)-2-hydroxy-3-isopropylamino-propane was reacted with Raney-nickel/$H_2$ to obtain 1-(3-aminophenoxy)-2-hydroxy-3-isopropylamino-propane having a melting point of 91–92° C.

EXAMPLE XXII

Preparation of 1-(4-cyanophenoxy)-2-hydroxy-3-isopropylamino-propane.HCl

Using the procedure of Example II, 1-(4-cyanophenoxy)-2,3-epoxy-propane was reacted with isopropylamine to form 1-(4-cyanophenoxy)-2-hydroxy-3-isopropylamino-propane. Its hydrochloride had a melting point of 157–159° C.

EAMPLE XXIII

Preparation of 1-(2-cyanophenoxy)-2-hydroxy-3-isopropylamino-propane.HCl 26.2 g. (0.15 mol) of 1-(2-cyanophenoxy)-2,3-epoxy-propane were dissolved in 150 ml. of ethanol and then 23.6 g. (0.4 mol) of isopropylamine were added thereto. After the mixture had stood for 10 hours at room temperature, it was heated at reflux for 3 hours. Then, the solvent was distilled off in vacuo, and the residue was taken up in dilute hydrochloric acid and the solution vacuum filtered from the insoluble matter. The aqueous acid phase was made alkaline with sodium hydroxide and the base precipitating in oily form was extracted several times with ether. The ether extracts were combined and dried over sodium sulfate and the ether was distilled off to obtain 26 g. of raw 1-(2-cyanophenoxy)-2-hydroxy-3-isopropylamino-propane. The product obtained was recrystallized from acetic acid ester with an addition of petroleum ether. The precipitate was dissolved in alcohol, admixed with ethereal HCl and the precipitating crystalline hydrochloride was filtered off. The melting point of the hydrochloride was 133–135° C.

EXAMPLE XXIV

Preparation of 1-(3-cyanophenoxy)-2-hydroxy-3-isopropylamino-propane.2HCl

Using the procedure of Example XXIII, 1-(3-cyanophenoxy)-2,3-epoxy-propane was reacted with isopropylamine to obtain 1-(3-cyanophenoxy)-2-hydroxy-3-isopropylamino-propane. Its maleinate had a melting point of 88 to 92° C.

EXAMPLE XXV

Preparation of 1-(2-methyl-5-aminophenoxy)-2-hydroxy-3-isopropylamino-propane.2HCl 13.4 g. (0.05 mol) of 1-(2-methyl-5-nitrophenoxy)-2-hydroxy-3-isopropylamino-propane were dissolved in 150 ml. of methanol and hydrogenated over Raney-nickel at room temperature and at atmospheric pressure. After the catalyst had been separated, the solvent was distilled in vacuo. The oily residue (8.6 g.=72% of theory) was dissolved in a small amount of methanol and admixed with ethereal hydrochloric acid. Then, the dihydrochloride salt precipitating in crystalline form was vacuum filtered and recrystallized from methanol with an addition of ether to obtain 10.7 g. (68.5% of theory) of 1-(2-methyl-5-amino phenoxy) - 2 - hydroxy - 3 - isopropylamino - propane dihydrochloride having a melting point of 240–241° C.

EXAMPLE XXVI

Preparation of 1-(2-methyl-4-cyanophenoxy)-2-hydroxy-3-isopropylamino-propane.HCl 26.4 g. (0.14 mol) of 1-(2-methyl-4-cyanophenoxy)-2,3-epoxy-propane were dissolved in 200 ml. of ethanol, and after an addition of 26.6 g. (0.45 mol) isopropylamine, the mixture was allowed to stand overnight at room temperature. Then, the mixture was first heated at about 60° C. for 2 hours and then it was heated at reflux for 1 hour, after which the solvent was distilled off in vacuo. The remaining residue was dissolved in dilute hydrochloric acid and was extracted with ether. The aqueous phase was separated and made alkaline with sodium hydroxide. The base precipitating in solid form was isolated and recrystallized from a mixture of ethyl acetate and petroleum ether. The base thus purified was dissolved in ethanol and admixed with ethereal hydrochloric acid to obtain 12.5 g. of 1 - (2-methyl-4-cyanophenoxy)-2-hydroxy-3-isopropylamino-propane hydrochloride in the form of a crystalline product having a melting point of 162–164° C.

EXAMPLE XXVII

Preparation of 1-(2-chloro-4-aminophenoxy-2-hydroxy-3-isopropylamino-propane.2HCl 7.25 g. (0.025 mol) of 1-(2-chloro-4-nitrophenoxy)-2-hydroxy-3-isopropylamino-propane were dissolved in 100 ml. of methanol and hydrogenated under atmospheric pressure and at room temperature with hydrogen and a Raney-nickel catalyst. After the catalyst had been removed, the solvent was distilled off in vacuo and the residue was dissolved in a small amount of methanol and admixed with ethereal hydrochloric acid. The crystalline precipitate was vacuum filtered and recrystallized from methanol/ether to obtain 4.5 g. (51% of theory) of 1-(2-chloro - 4 - aminophenoxy) - 2 - hydroxy - 3 - isopropylamino propane dihydrochloride having a melting point of 210–212° C.

EXAMPLE XXVIII

Preparation of 1-(3-methyl-4-aminophenoxy)-2-hydroxy-3-isopropylamino-propane.2HCl 6.7 g. (0.025 mol) of 1-(3-methyl-4-nitrophenoxy-2-hydroxy-3-isopropylamino-propane were dissolved in 70 ml. of ethanol and hydrogenated with a Raney-nickel catalyst at room temperature under atmospheric pressure. After the catalyst had been removed, the solvent was distilled off in vacuo and the solid residue was recrystallized from a mixture of ethyl acetate and petroleum ether. The crystalline base was vacuum filtered and dissolved in a small amount of methanol. Then, ethereal hydrochloric acid was added thereto and the crystals formed were isolated and dried to obtain 4 g. of 1-(3-methyl-4-aminophenoxy)-2-hydroxy-3-isopropylamino-propane dihydrochloride having a melting point of 248–251° C.

EXAMPLE XXIX

Preparation of 1-(2-methyl-5-cyanophenoxy)-2-hydroxy-3-isopropylamino-propane.HCl 21.5 g. (0.114 mol) of 1-(2-methyl-5-cyanophenoxy)-2,3-epoxy-propane were dissolved in 200 ml. of methanol and then, 23.6 g. (0.4 mol) of isopropylamine were added thereto. After the mixture had stood for 1 hour at room temperature, it was heated at reflux for 2.5 hours. Then, the solvent was distilled off in vacuo, and the solid residue was recrystallized from ethyl acetate by an addition of petroleum ether (boiling point=40° C.). The colorless crystalline base was dissolved in methanol, ethereal hydrochloric acid was added and after an addition of absolute ether, 12.5 g. of the crystalline 1-(2-methyl-5-cyanophenoxy)-2 - hydroxy - 3 - isopropylamino - propane hydrochloride having a melting point of 165–168° C. were obtained.

EXAMPLE XXX

Preparation of 1-(2-amino-4-chlorophenoxy)-2-hydroxy-3-isopropylamino-propane.2HCl 6.4 g. (0.022 mol) of 1-(2-nitro-4-chlorophenoxy)-2-hydroxy-3-isopropylamino-propane were dissolved in 100 ml. of methanol and hydrogenated over Raney-nickel at atmospheric pressure and at room temperature. After the Raney-nickel had been vacuum filtered off, the methanol was distilled off in vacuo. The residue was dissolved in methanol, acidified with ethereal hydrochloric acid and a small amount of ether was added thereto to obtain 5.3 g. of 1-(2-amino-4-chlorophenoxy)-2-hydroxy-3-isopropylamino-propane dihydrochloride having a melting point of 243–247° C.

EXAMPLE XXXI

Preparation of 1-(2-cyano-3-methylphenoxy)-2-hydroxy-3-isopropylamino-propane.HCl Using the procedure of Example XXX, 1-(2-cyano-3-methylphenoxy)-2,3-epoxy-propane in ethanol was reacted with isopropylamine to obtain 1-(2-cyano-3-methylphenoxy)-2-hydroxy-3-isopropylamino-propane. Its hydrochloride had a melting point of 173–176° C.

EXAMPLE XXXII

Preparation of 1-(3-amino-4-methylphenoxy)-2-hydroxy-3-isopropylamino-propane.HCl Using the procedure of Example XXVIII, 1-(3-nitro-4-methylphenoxy)-2-hydroxy-3-isopropylamino - propane was hydrogenated in ethanol with a Raney-nickel catalyst to obtain 1-(3-amino-4-methylphenoxy)-2-hydroxy-3-isopropylamino-propane. Its dihydrochloride had a melting point of 216–218° C.

EXAMPLE XXXIII

Preparation of 1-(2-chloro-4-cyanophenoxy)-2-hydroxy-3-isopropylamino-propane.HCl Using the procedure of Example XXX, 1-(2-chloro-4-cyanophenoxy)-2,3-epoxy-propane was reacted with isopropylamine to obtain 1-(2-chloro-4-cyanophenoxy)-2-hydroxy-3-isopropylamino-propane. Its hydrochloride had a melting point of 134–136° C.

EXAMPLE XXXIV

Preparation of 1-(3-cyano-4-methylphenoxy)-2-hydroxy-3-isopropylamino-propane.HCl Using the procedure of Example XXX, 1-(3-cyano-4-methylphenoxy)-2,3-epoxy-propane was reacted with isopropylamine to obtain 1-(3-cyano-4-methylphenoxy)-2-hydroxy-3-isopropylamino-propane. Its hydrochloride had a melting point of 160–162° C.

EXAMPLE XXXV

Preparation of 1-(3-methyl-5-cyanophenoxy)-2-hydroxy-3-isopropylamino-propane.HCl Using the procedure of Example XXX, 1-(3-methyl-5-cyanophenoxy)2,3-epoxy-propane was reacted with isopropylamine in ethanol to obtain 1-(3-methyl-5-cyanophenoxy)-2-hydroxy-3-isopropylamino-propane.

The compounds according to the present invention, that is, those embraced by Formulas I and Ia above and their non-toxic, pharmacologically acceptable acid addition salts, have useful pharmacodynamic properties. More particularly, they produce bradycardia and at the same time act as N-isopropyl-noradrenaline (Isoproterenol) antagonists. Thus, the tachycardiac effects caused by the administration of N-isopropyl-noradrenaline are suppressed or eliminated by prior administration of one of the compounds of the present invention, and cardiac arrhythmia are equalized by them. In other words, the compounds according to the present invention block the sympathetic nervous system of the heart, which has heretofore not been possible with chemotherapeutic agents. Consequently, the areas of indication for the compounds of the present invention are hypertension, angina pectoris, cardiac arrhythmia, digitalis intoxication and pheochromocytoma disorders.

In view of the presence of an asymmetric carbon atom in the 2-position of the propylene chain, the compounds of the present invention exist not only in the form of racemic mixtures but also in the form of optical antipodes. The optical antipodes may be separated from the racemates by conventional methods and have the same pharmacodynamic properties as the racemates.

For therapeutic purposes in warm-blooded animals, the compounds of the present invention are administered perorally or parenterally as active ingredients in conventional dosage unit compositions, that is, compositions in dosage unit form consisting essentially of a major amount of an inert pharmaceutical carrier and one dosage unit of the active ingredient. Dosages of the compounds pursuant to the present invention is from 0.01 to 5 mgm./kg., depending upon the route of administration and the intensity of the effect desired or required. Thus, for oral administration the dosage range is 0.4–5 mgm./kg., preferably 1–3 mgm./kg., for intravenous administration it is 0.01–0.2 mgm./kg., preferably 0.02–0.1 mgm./kg.; and for subcutaneous administration it is 0.02–1.0 mgm./kg., preferably 0.1–0.3 mgm./kg. Typical examples of dosage compositions are tablets, coated pills, suspensions, solutions, suppositories and the like.

EXAMPLE XXXVI 40.0 g. of racemic 1-(2-cyanophenoxy)-2-hydroxy-3-isopropylamino-propane hydrochloride, 16.40 g. of corn starch, 240.0 g. of calcium phosphate and 1.0 g. of magnesium stearate were thoroughly admixed and then granulated in the conventional manner. The granulate was then pressed into 1,000 tablets weighing 445 mg. each and containing 40 mg. of the active ingredient.

EXAMPLE XXXVII 25.0 g. of (-)-1-(2-cyanophenoxy)-2-hydroxy-3-isopropylamino-propane hydrochloride and 175 g. of corn starch were thoroughly admixed. The mixture was then used to fill gelatin capsules with 200 mg. of the mixture. Each capsule contained 25 mg. of the optically active ingredient.

EXAMPLE XXXVIII 2.5 parts by weight of racemic 1-(2-cyano-3-methylphenoxy) - 2 - hydroxy-3-isopropylamino-propane hydrochloride and 0.2 part by weight of sodium salt of ethylene diamine tetracetic acid were dissolved in distilled water and the volume was adjusted to 100 parts. The solution was filtered until free from suspended particles and filled into 1 cc. ampoules under aseptic condition. The ampoules were sterilized and sealed. Each ampoule contained 25 mg. of the active ingredient.

EXAMPLE XXXIX 25.0 g. of racemic 1-(2-allyl-4-cyanophenoxy)-2-hydroxy-3-isopropylamino-propane maleinate, 295.0 g. of carboxymethyl cellulose and 20.0 g. of stearic acid were thoroughly admixed and the mixture was granulated using a solution of 40.0 g. of cellulose acetatephthalate in 200 ml. of an ethanol and ethyl acetate mixture. The granulate was then pressed into cones weighing 380 mg. which were coated with a sugary 5% solution of polyvinylpyrrolidone in water in the usual fashion. Each coated pill contained 25 mg. of active ingredient.

EXAMPLE XL 50.0 g. of 1-(4-cyanomethylphenoxy)-2-hydroxy-3-isopropylamino-propane sulfate, 16.40 g. of lactose, 194.0 g. of corn starch, 14.0 g. of colloidal silicic acid and 6.0 g. of polyvinylpyrrolidone were thoroughly admixed and the mixture was granulated with an aqueous solution containing 10 g. of soluble starch in the usual manner. The granulate was admixed with 2.0 g. of magnesium stearate and pressed into 440 mg. tablets containing 50 mg. of the active ingredient.

Although the above illustrative dosage unit compositions comprise only a few of the compounds of the present invention as an active ingredient, it should be understood that any of the other compounds embraced by Formulas I and Ia or a non-toxic acid addition salt thereof, either in the racemic or in the optically active d- or l-form, may be substituted therefor in Examples 36–40. Moreover, the amounts of the active ingredient in the illustrative examples may be varied within the indicated limits to meet particular requirements, as may the amounts and nature of the inert ingredients.

We claim:

1. A compound selected from the group consisting of racemic 1-phenoxy-2-hydroxy-3-isopropylaminopropanes of a formula

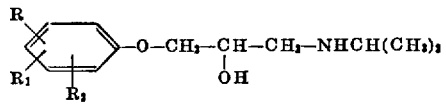

wherein R is selected from the group consisting of hydrogen, chlorine, bromine, alkyl of 1 to 4 carbon atoms, alkoxy of 1 to 4 carbon atoms, alkenyl of 2 to 4 carbon atoms and cyano, $R_1$ is $—(CH_2)_x—CN$, x is an integer from 0 to 3 and $R_2$ is selected from the group consisting of hydrogen, chlorine, bromine, alkyl of 1 to 4 carbon atoms and alkoxy of 1 to 4 carbon atoms, their optically active isomers and non-toxic, pharmaceutically acceptable acid addition salts of said racemates and of said optically active isomers.

2. A compound of claim 1 wherein R is methyl, $R_1$ is $—(CH_2)_x—CN$, x is 0 and $R_2$ is hydrogen.

3. A compound of claim 1 wherein R and $R_2$ are hydrogen, $R_1$ is $—(CH_2)_x—CN$ and x is 0.

4. A compound of claim 1 wherein R is methyl, $R_1$ is $—(CH_2)_x—CN$, x is 1 and $R_2$ is hydrogen.

5. A compound of claim 1 wherein R and $R_2$ are hydrogen and $R_1$ is $—(CH_2)_x—CN$ and x is 1.

6. A compound of claim 1 which is selected from the group consisting of racemic 1-(2-cyanophenoxy)-2-hydroxy-3-isopropylamino-propane, its optically active isomers and the non-toxic, pharmaceutically acceptable acid addition salts of said racemate and optically active isomers.

7. A compound of claim 1 which is selected from the group consisting of racemic 1-(2-cyano-3-methylphenoxy)-2-hydroxy-3-isopropylamino-propane, its optically active isomers and non-toxic, pharmaceutically acceptable acid addition salts of said racemate and optically active isomers.

8. A compound of claim 1 which is selected from the group consisting of racemic 1-(2-methyl-5-cyano[methyl]phenoxy)-2-hydroxy-3-isopropylamino-propane, its optically active isomers and non-toxic, pharmaceutically acceptable acid addition salts of said racemate and optically active isomers.

9. A compound of claim 1 which is selected from the group consisting of racemic 1-(3-cyano-4-methylphenoxy)-2-hydroxy-3-isopropylamino-propane, its optically active isomers and non-toxic, pharmaceutically acceptable acid addition salts of said racemate and optically active isomers.

10. A compound of claim 1 which is sselected from the group consisting of racemic 1-(2-methyl-4-cyanophenoxy) - 2 - hydroxy-3-isopropylamino-propane, its optically active isomers and non-toxic, pharmaceutically acceptable acid addition salts of said racemate and optically active isomers.

References Cited

The following references, cited by the Examiner, are of record in the patented file of this patent or the original patent.

UNITED STATES PATENTS

| | | | |
|---|---|---|---|
| 2,642,436 | 6/1953 | Clinton et al. | 260—465 X |
| 2,642,437 | 6/1953 | Clinton et al. | 260—465 X |
| 3,644,469 | 2/1972 | Koppe et al. | 260—465 E |

(Other references on following page)

UNITED STATES PATENTS

| | | | |
|---|---|---|---|
| 3,663,607 | 5/1972 | Barrett et al. | 260—465 E |
| 3,542,872 | 11/1970 | Koppe et al. | 260—465 E |
| 3,541,130 | 11/1970 | Koppe et al. | 260—465 E |
| 3,515,741 | 6/1970 | Thoma et al. | 260—465 E |
| 3,547,974 | 12/1970 | Troxler et al. | 260—465 E |

OTHER REFERENCES

Lundsford et al., Journal of the American Chemical Society, vol. 82, pp. 1166–1171 (1960).

Petrow et al., Journal of Pharmacy and Pharmacology, vol. 5, pp. 359–369 (1953).

JOSEPH P. BRUST, Primary Examiner

U.S. Cl. X.R.

260—253, 307, 340, 343, 348, 471, 501, 465 D, 519, 570; 424—253, 282, 304, 309, 319, 330